United States Patent [19]
Lee et al.

[11] Patent Number: 5,630,418
[45] Date of Patent: May 20, 1997

[54] NOISE CONTROLLER FOR AUTOMATICALLY DETECTING AND ATTENUATING BREAK NOISE IN A PORTABLE HAND HELD DOPPLER FETAL HEART BEAT PROBE

[75] Inventors: William C. Lee, Orinda; Delmer D. Fisher, Santa Cruz; Andras Boross, Belmont, all of Calif.

[73] Assignee: MedaSonics, Inc., Fremont, Calif.

[21] Appl. No.: 662,055

[22] Filed: Jun. 12, 1996

[51] Int. Cl.$^6$ ........................................... A61B 8/00
[52] U.S. Cl. ........................................... 128/661.07
[58] Field of Search .................. 128/660.01, 660.07, 128/660.1, 661.07, 661.08, 661.09, 662.01

[56] References Cited

U.S. PATENT DOCUMENTS

| | | | |
|---|---|---|---|
| 4,603,702 | 8/1986 | Hwang | 128/660.01 |
| 4,694,680 | 9/1987 | Takeuchi et al. | 128/660.01 |
| 5,517,994 | 5/1996 | Burke et al. | 128/660.07 |

*Primary Examiner*—George Manuel
*Attorney, Agent, or Firm*—Fliesler, Dubb, Meyer & Lovejoy

[57] ABSTRACT

A noise controller for use in a probe in a hand held ultrasonic Doppler fetal heart beat detection and monitoring system where the probe includes a crystal for generating an input signal as a function of the ultrasonic energy in received ultrasonic wave and a detector for generating a first signal from the input signal. The noise controller comprises a volume controller for receiving the first signal and for processing the first signal to produce an analog signal as the output of the probe. A detector generates a second signal whenever break noise is detected in the first signal. A muting circuit immediately lowers the amplitude of the analog signal upon detection of break noise by the detector thereby substantially attenuated in the analog signal the break noise which occurred in the first signal.

7 Claims, 5 Drawing Sheets

NOISE CONTROLLER FOR AUTOMATICALLY DETECTING AND ATTENUATING BREAK NOISE IN A PORTABLE HAND HELD DOPPLER FETAL HEART BEAT PROBE

BACKGROUND OF THE INVENTION

1. Field of the Invention

The present invention relates to a portable, hand held probe in a Doppler fetal heart beat detection and monitoring system for detecting the fetal heart beat using Doppler ultrasound techniques and more specifically to a method and a noise controller within the probe capable for reducing break noise associated with the application of acoustic coupling gel to the probe and the momentary interruption in the probe/gel/skin interface associated with the movement of the probe across the skin during usage of the probe.

2. Description of the Related Art

The Doppler effect was first described in the 19th century by Christian Doppler, an Austrian scientist from Salzburg. A hand held ultrasonic Doppler fetal heart beat detection and monitoring system includes a probe for detecting the fetal heart beat and for providing an analog signal to a headset and/or to an auxiliary unit (hereinafter referred to as a Calc. unit). The probe includes one or more crystals that transmits and receives ultrasonic sound waves. In use, the detector is held against the mothers abdomen and directed towards the fetus. The transmitter crystal generates an ultrasonic wave that passes into the mothers body. The transmitted ultrasonic wave is reflected by the movement of the fetal heart as a reflected ultrasonic wave to the receiving crystal. The frequency of reflected ultrasonic wave is changed as a function of the velocity of movement of the fetal heart. This frequency shift is detected and processed by the probe into an analog signal that can be heard as the fetal heart beat through the headset and the speaker in the Calc. unit. The Calc. unit also processes the analog signal to derive a fetal heart rate and displays the same.

A probe 11 having a single energy level transmitter and a detector 51, volume controller 52 and power supply 54 of FIG. 2 is available from MedaSonics, Inc. as Part No. 101-0135-010. A Calc. unit suitable for use with probe 11 is available from MedaSonics, Inc., 47233 Fremont Boulevard, Fremont, Calif., 94538, and is identified as FETAL CALC. SPEAKER/HEART DISPLAY, Part No. 101-0238-010. A headset 10 compatible for use with probe 11 can also be purchased from MedaSonics, Inc., and is identified as HEADSET, Part No. 101-0008-010.

During the later stage of the first trimester and the early stage of the second trimester, the heart of the fetus is so small that the conventional hand held Doppler fetal heart beat detection and monitoring systems encounter difficulty in detecting the fetal heart beat due to the very low level of ultrasonic energy in the reflected ultrasonic wave from the fetal heart.

One approach to this problem was to provide a set of interchangeable probes where each probe emits ultrasound energy at a different ultrasonic frequency to improve the sensitivity of the probe in detecting the fetal heart beat. The disadvantage of this solution is that the user has to have easy and immediate access to the set of probes, the necessity of physically having to change the probes during the examination, the potential of one or more probes being damaged and the increase cost of having more than one probe.

Other approaches have been directed to methods of processing of the reflected ultrasonic wave by the detector in the probe to distinguish the low level fetal heart beat component from the noise component of the reflected ultrasonic waves.

Typically a medium, such as an aqueous based acoustic gel or petroleum based gelatin, is applied to the probe. The medium acts as an acoustic impedance matching interface between the probe and the insonated area, which is the skin surface. Application of the medium to the probe generates unwanted noise, referred to as break noise, which appears as a high amplitude signal component in the output signal of the detector and is heard as a loud sound in the head set or from a speaker in the Calc. unit. Break noise is also generated when the probe is moved across the skin surface causing the probe/medium/skin interface to be broken.

SUMMARY OF THE INVENTION

An object of the present invention is to provide a probe for use in a hand held Doppler fetal heart beat detection and monitoring system that will automatically detect and attenuate break noise.

The present invention is a method and noise controller within a probe in a hand held Doppler fetal heart beat detection and monitoring system for automatically detecting the occurrence of break noise and for attenuating the portion of the analog signal from the probe associated with break noise. The probe comprises a receiving crystal for receiving reflected ultrasonic energy of the reflected ultrasonic wave, a detector for generating an output signal as a function of the received ultrasonic energy, a detector for automatically detecting break noise in the output signal, means for attenuating the break noise in the analog signal from the probe. Specifically, the noise controller includes a comparator that monitors the output signal from the detector for high amplitude values in the output signal above a reference amplitude value, the occurrence of which indicates the presence of break noise. A microcontroller is included which monitors the output of the comparator and whenever the presence of break noise is indicated by the output of the comparator, the microcontroller causes the gain of a variable gain amplifier, which amplifies the output signal from the detector to produce the analog signal, to be immediately lowered thereby attenuating that portion of the analog signal containing the break noise.

BRIEF DESCRIPTION OF THE DRAWINGS

The invention will be described with respect to the particular embodiments therefore and reference will be made to the drawings, in which.

DETAILED DESCRIPTION OF THE INVENTION

Figure 1:
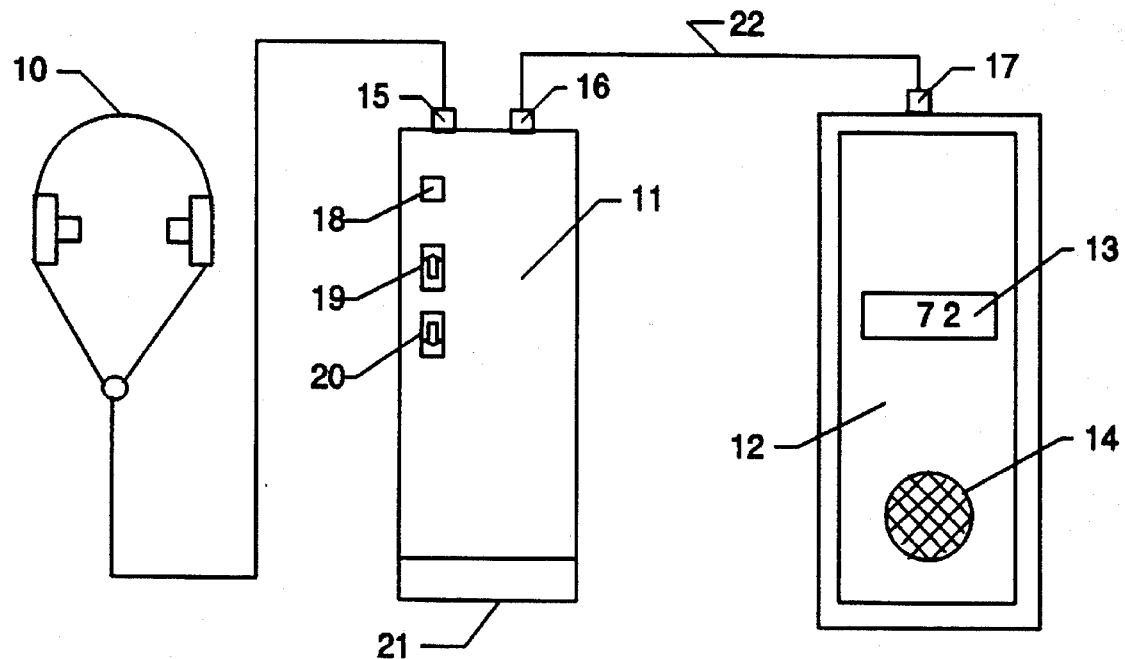
FIG. 1 is an illustration depicting a hand held Doppler fetal heart beat detection and monitoring system including the probe of the invention.

FIG. 1 illustrates an ultrasonic Doppler fetal heart beat detection and monitoring system embodying a probe 11, a head set 10 and a Calc. unit 12. Probe 11 generates ultrasonic waves and then receives and processes reflected ultrasonic waves to generate an analog signal of the fetal heart beat. Probe 11 also includes a power button 18, volume down button 19 and a volume up button 20. The volume level of the sound generated by headset 10 and speaker 14 in Calc. unit 12 is controlled by volume buttons 19 and 20. Crystals that produce and receive ultrasonic waves are located in the base 21 of probe 11. Headset 10 is connected to probe 11 via jack 15 for receiving the analog signal and for generating an audible fetal heart beat. Calc. unit 12 is connected to probe 11 by multi-line cable 22 via plugs 16 and 17 and includes electronic circuitry for processing the analog signal from probe 11 into an audio fetal heart beat which is emitted from speaker 14 and further calculates and displays the fetal heart rate on a display means 12.

A fetal stethoscope is formed by the combination of probe 11 and headset 10 or probe 11 and Calc. unit 12. Headset 10 allows the doctor to solely hear the fetal heart beat during an examination. Calc. unit 12 is used when the doctor wishes the patient to hear the fetal heart beat and/or when the doctor wishes to obtain a read-out on the fetal heart rate.

In use a medium, typically an aqueous based acoustic gel or petroleum based gelatin is applied to base 21 of probe 11. The medium acts as an acoustic impedance matching device to aid in the transmission of ultrasonic waves generated by probe 11 into the body of the mother and in the transmission of reflected ultrasonic waves from the mother, such as the fetal heart, to probe 11. Probe 11 is then placed against the outer skin of the mother with the medium between the probe and the skin. Ultrasonic waves generated by a crystal within probe 11 enters the mothers body. The transmitted ultrasonic waves are reflected by the movement of the fetal heart which changes the frequency of the ultrasonic wave as a function of the velocity of movement of the fetal heart. The energy level of the reflected ultrasonic wave from the fetal heart is directly proportional to the energy level of the transmitted ultrasonic wave from probe 11. The reflected ultrasonic waves pass through the medium and are sensed by a second crystal in probe 11.

It has been found that the energy of other reflected ultrasonic waves from within the mother's body, which is referred to as tissue clutter, is independent of the energy level of ultrasonic waves transmitted by probe 11. Further, the internal noise generated by the electronics within probe 11 is, for the most part, independent of the energy level of ultrasonic waves being generated by crystal 50. A first approximation for the signal to noise ratio of the probe 11 is derived from the magnitude of the noise generated by tissue clutter, the magnitude of the noise generated by the electronics within probe 11 and the magnitude of the energy of the reflected ultrasonic wave from the fetal heart. Therefore an increase in the ultrasonic power in the transmitted ultrasonic wave will increase the signal to noise ratio of the probe in that the energy level of the reflected ultrasonic wave from the fetal heart will be increased while tissue clutter noise and noise generated in the probe will remain at the same level. Tests have shown that by increasing the energy level of the transmitted ultrasonic wave by 6 dB that the signal to noise ratio will be increase by approximately 6 dB.

Figure 2:
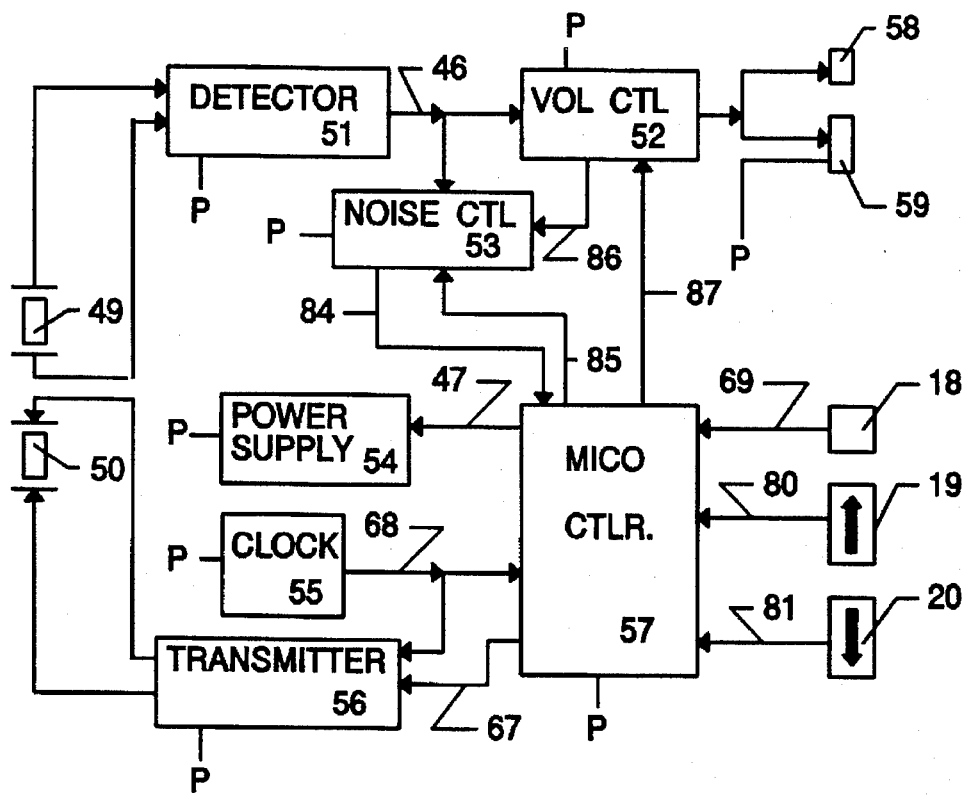
FIG. 2 is a block diagram of the probe of the invention.

FIG. 2 is a block diagram of the major components within probe 11. A transmitter 56 drives crystal 50 at a frequency of the square wave clock signal of clock 55. Microcontroller 57 is commercially available from Microchip Technology, Inc., 2355 West Chandler Blvd, Chandler, Ariz. 85224, as part number PIC 16C622. Microcontroller 57 provides a transmitter power setting signal on bus 67 to transmitter 56 for setting the power level of transmitter 56. Power supply 54 receives a power off signal on line 47 from microcontroller 57 which places microcontroller 57 in a SLEEP state and turns off power to the other components within probe 11. Power supply 54 receives a power on signal on line 47 from microcontroller 57 which places microcontroller 57 in a WAKE state and turns on power to the other components within probe 11. In the SLEEP state, microcontroller 57 monitors power button 18 and upon sensing the depression of power button 18 will send the power on signal to power supply 54.

Receiving crystal 49 responds to the reflected ultrasonic energy in the reflected ultrasonic waves and provides a input signal, derived from the received reflected ultrasonic energy, to detector 51. Detector 51 is well known in the art and examples of detector 51 are provided in Section 14 of the Electronics' Engineers Handbook, Donald G. Fink and Donald Christiansen, McGraw Hill Book Company, 1989, ISSN 0-07-020982-0.

The output signal of detector 51 is provided on line 46 to a volume controller 52 that in turn provides an analog signal at sockets 58 and 59. Socket 58 receives jack 15 from headset 10 and socket 59 receives plug 16 on cable 22 from Calc. unit 12. Socket 59 also provides power from power supply 54 via cable 17 to Calc. unit 12. Microcontroller 54 generates a pulse width modulated signal on line 87 to volume controller 52 for controlling the amplitude of the analog signal generated by volume controller 52. When the volume down button 19 is depressed, the pulse width of the pulse width modulated signal is decreased, thereby causing the amplitude of the analog signal from volume controller 52 to be decreased. Similarly, when the volume up button 20 is depressed, the pulse width of the width modulation signal is increased thereby causing the amplitude of the analog signal from volume controller 52 to be increased.

A noise controller 53 is provided for detecting break noise. Microcontroller 57 monitors the output of noise controller 53 on line 84 and upon sensing break noise being detected by noise controller 53 generates a signal on line 85 to noise controller 53 that activates circuitry within noise controller 53 for reducing the amplitude of the analog signal from volume controller 52.

Figure 3:
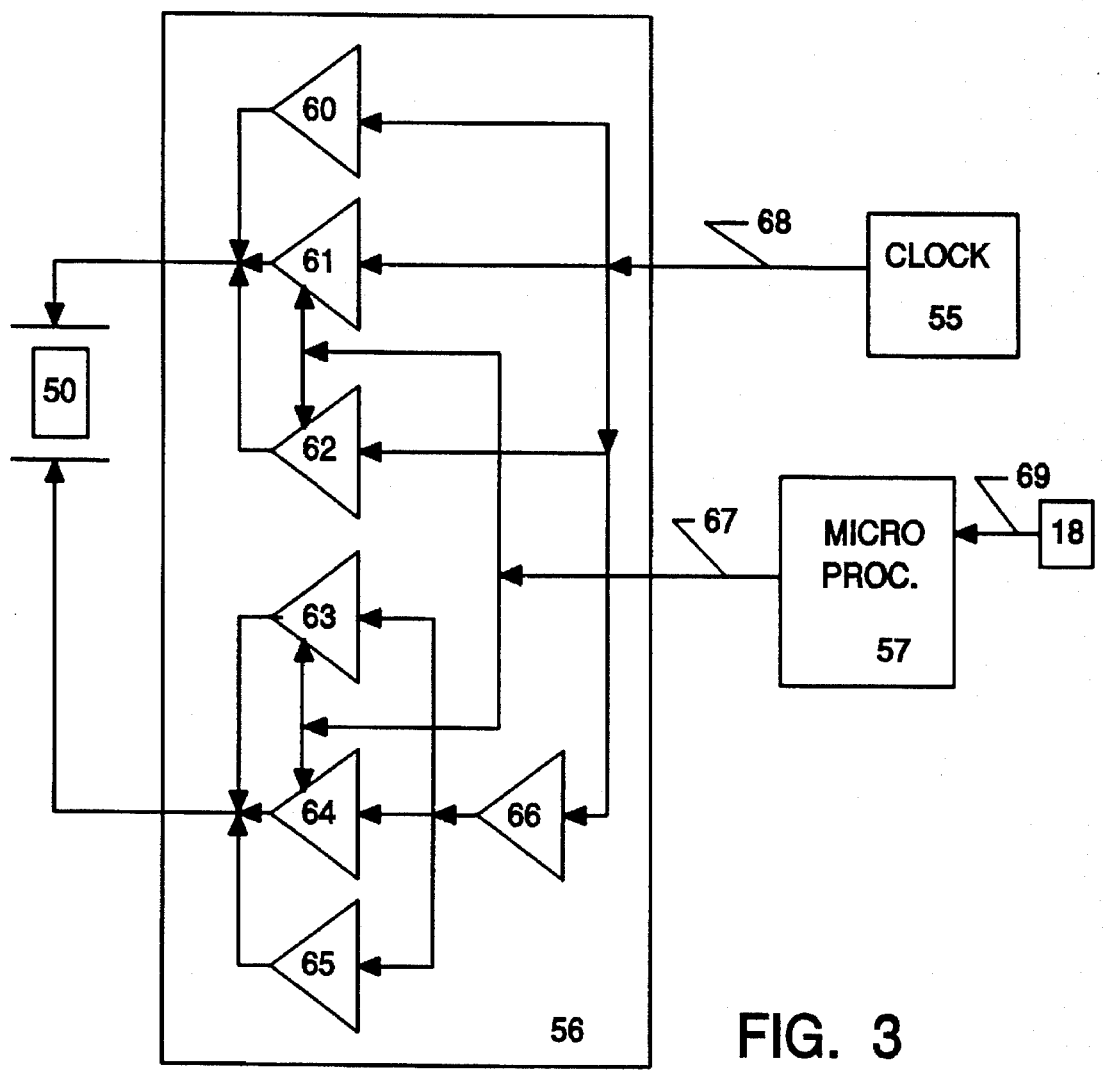
FIG. 3 is a block diagram of a plurality of selective power drivers for driving the transmitting crystal at two different power settings.

FIG. 3 is a block diagram of the transmitting portion of probe 11. Transmitter 56 consists of six power drivers 60, 61, 62, 63, 64 and 65 connected in pairs, where each power drive is an AC or ACT logic tri-state inverting buffer. Drivers 60 and 65 are a first pair, drivers 61 and 64 are a second pair, and drivers 62 and 63 are a third pair. Transmitter 56 is a continuous wave (CW) transmitter. Clock 56 provides a square wave clock signal via line 68 to drivers 60, 61 and 62 and to inverter 66 that in turn provides the inverted square wave clock signal to drivers 63, 64 and 65. When power is turned on drivers 60 and 65 are always activated and providing a driving signal to crystal 50. When the square wave clock signal is high driver 60 will act as a current source and driver 65 will act as a current sink and when the square wave clock signal is low driver 60 will act as a current sink and driver 65 will act as a current source. This results in crystal 50 generating an ultrasonic wave at the frequency of the square wave clock signal appearing on line 68 from clock 55. The energy or strength of the ultrasonic wave created by crystal 50 is a function of the magnitude of the power or current driving crystal 50.

Microcontroller 57 monitors the state of power button 18 via line 69. The low power mode is selected by holding down power button 18 for a first period of time and the high power mode is selected by holding down the power button 18 for a second period of time, where the first period is shorter than the second period. When microcontroller 59 determines that power button 18 was depressed for the second period of time for the high power mode, microcontroller 57 conditions drivers 61, 62, 63 and 64 via a signal on line 67. Drivers 61 and 62 are in parallel with driver 60 and drivers 63 and 64 are in parallel with driver 65. When drivers 61, 62, 63 and 64 are activated, the power driving crystal 50 is increased by a factor of four which adds 6 dB to the energy of the ultrasonic wave being transmitted by probe 11.

Figure 4:
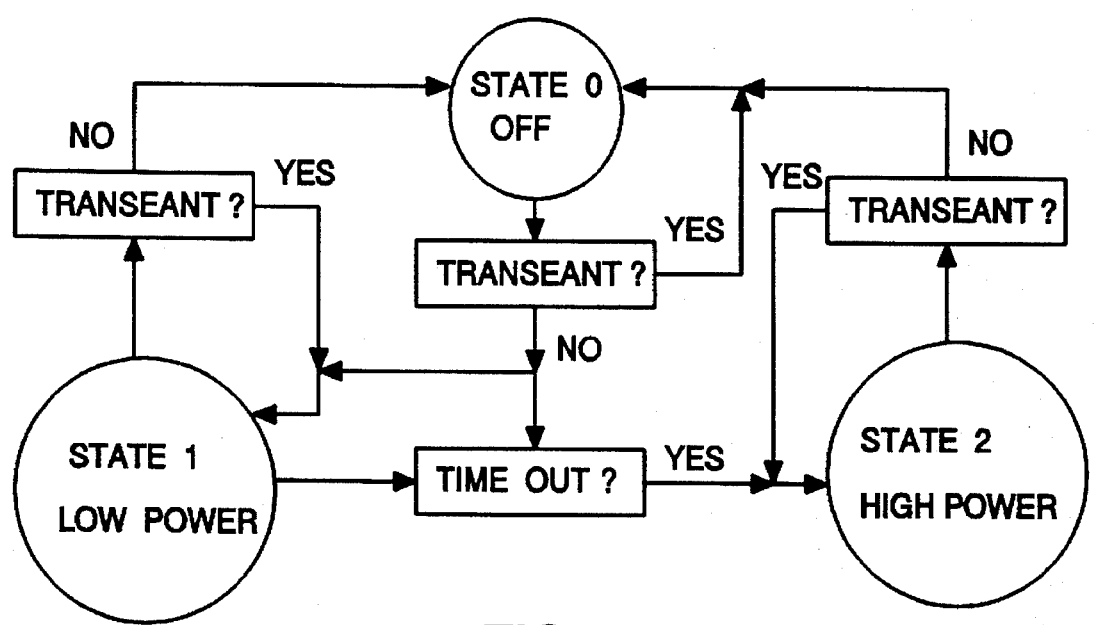
FIG. 4 is a state diagram illustrating the sequence of steps for the selection of one of the two power modes for the probe of the invention.

FIG. 4 is a state diagram illustrating the process that microcontroller 57 follows when monitoring power button 18. Starting with probe 11 in STATE 0, the off state, when power button 18 is depressed microcontroller 57 will start a timer to assess whether the incoming signal generated by the depressing of power button 18 is a transient signal. Whenever microcontroller determines the occurrence of a transient signal the STATE of probe 11 will not be changed. The remaining discussion will be made assuming that the signal generated by depressing the power button 18, the volume downbutton 19 and the volume up button 20 is a non transient signal.

When microcontroller 57 determines that signal generated by the depression of power button 18, microcontroller 57 will switch probe 11 to STATE 1, low power state, resulting in crystal 50 being driven only by drivers 60 and 65. The microcontroller 57 will continue to monitor the period that power button 18 is depressed after entering STATE 1 and if the power button 18 has been held down for the second period the microcontroller 57 will switch the probe 11 STATE 1, low power, to STATE 2, high power. This task is accomplished by microcontroller 57 initiating a counter with a count value of the second period when probe 11 is in STATE 0, off state, and power button 18 is first depressed and then counts down that counter for as long as the power button 18 remains depressed. If the counter reaches zero indicating the end of the second period, microcontroller 57 will switch probe 11 from STATE 1, low power, to STATE 2, high power by issuing a signal on line 67 that will turn on drivers 61, 62, 63 and 64 effectively placing drivers 61 and 62 in parallel with driver 60 and drivers 63 and 64 in parallel with driver 65. When drivers 61, 62, 63 and 64 are not in the on state in response to the signal on line 67 from microcontroller 57, the four drivers 61, 62, 63 and 64 are in a high impedance state rather than in an off state. If power button 18 is released prior to the counter reaching zero, then the probe 11 will remain in STATE 1, low power. When probe 11 is in either STATE 1 or STATE 2 and microcontroller 57 again detects that power button 18 is depressed, microcontroller 57 will switch probe 11 to STATE 0, off state.

With this sequence of operation for probe 11, probe 11 can go from the off state to the low power state, or from the off state through the low power state to the high power state. Probe 11 cannot switch between the low power state and the high power state without going through the off state.

Figure 5:
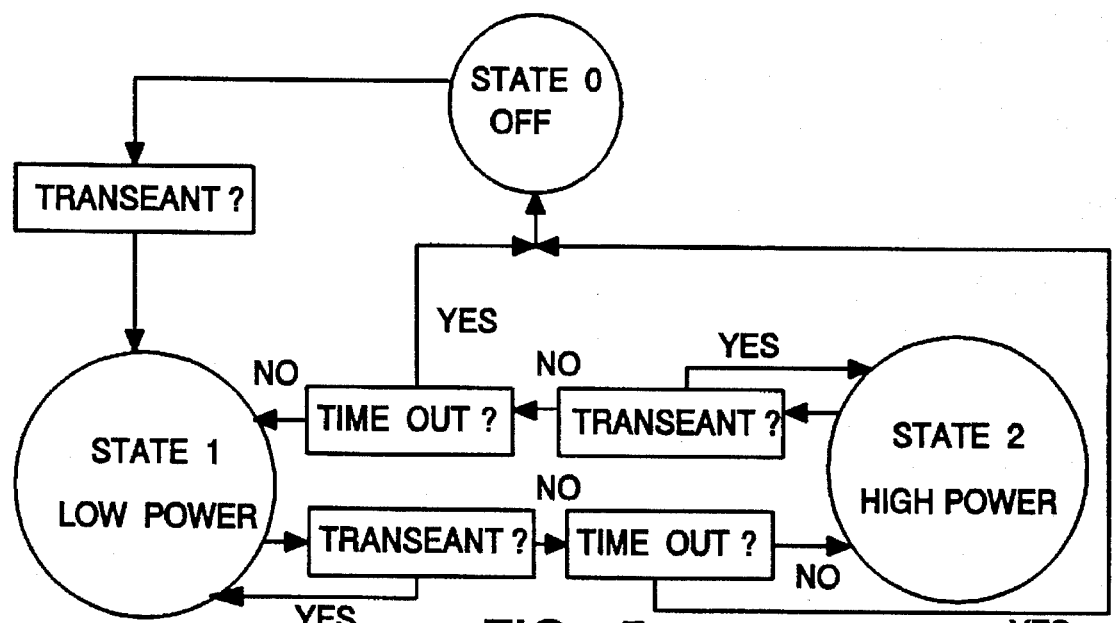
FIG. 5 is a state diagram illustrating another sequence of steps for the selection of one of the two power modes for the probe of the invention.

FIG. 5 is a alternate state diagram illustrating the process that microcontroller 57 follows when monitoring power button 18. Again, assuming that probe 11 is in STATE 0, off state, microcontroller 57 sensing the depressing of power button 18 switches probe 11 from STATE 0 to STATE 1, low power. Upon the next depression of power button 18, microcontroller 57 enters into a time-out phase. Microcontroller 57 loads a counter with a count for recognizing a request for STATE 0, the off state, and counts down the counter as long as the power button 18 is depressed. If the counter does not reach zero before the power button 18 is released then the microcontroller 57 will switch probe 11 from STATE 1, low power, to STATE 2, high power. If the counter reaches zero before the power button 18 is released, then microcontroller 57 will switch probe 11 from STATE 1, low power, to STATE 0, off.

If the probe 11 is in STATE 2, high power, and power button 18 is depressed, microcontroller 57 will enter into the time-out phase. The microcontroller 57 again loads the counter and counts down the counter as long as the power button 18 is depressed. If the counter does not reach zero before the power button 18 is released then the microcontroller 57 will switch probe 11 from STATE 2, high power, to STATE 1, low power. If the counter reaches zero before the power button 18 is released, then microcontroller 57 will switch probe 11 from STATE 2, high power, to STATE 0, off.

With this sequence of operation, probe 11 can switch back and forth between the high power and low power states without first passing through the off state.

Figure 6:
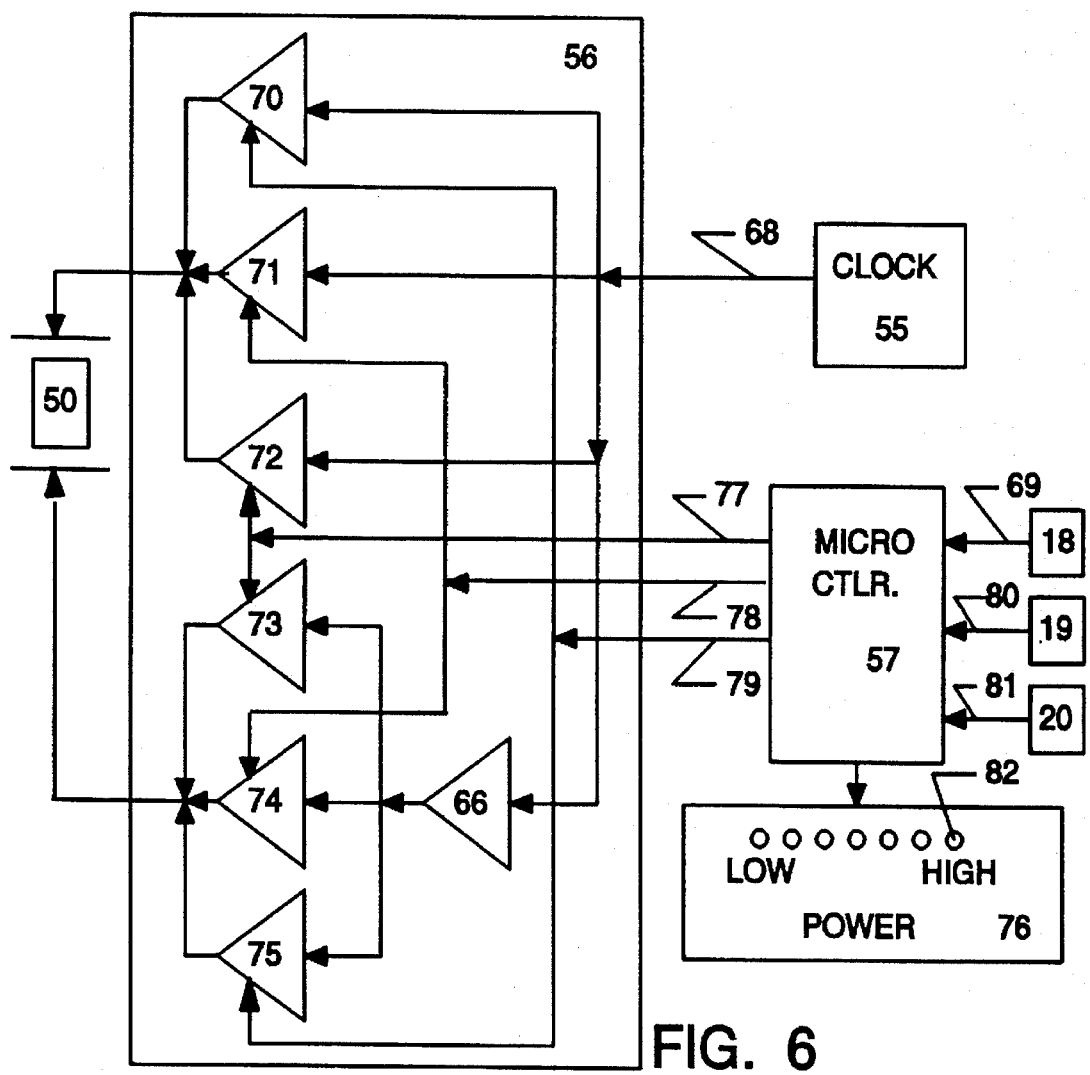
FIG. 6 is a block diagram of a plurality of selective power drivers for driving the transmitting crystal at seven different power settings.

FIG. 6 is an alternate embodiment of the transmitting portion of probe 11. Transmitter 56 is again shown as having six power drivers 70, 71, 72, 73, 74 and 75 connected in pairs where each power driver is an AC or ACT logic tri-state inverting buffer. Drivers 70 and 75 will drive crystal 50 with one unit of ultrasonic energy, drivers 71 and 74 will drive crystal 50 with two units of ultrasonic energy and drivers 72 and 73 will drive crystal 50 with four units of ultrasonic energy. By selecting the power driver pairs that are active, the energy driving crystal 50 can be between one unit and seven units of ultrasonic energy. Again clock 50 produces a square wave clock signal on line 68 connected directly to drivers 70, 71 and 72 and to drivers 73, 74, 75 through inverter 66. Again, when any of the drivers are not selected that driver will be in the high impedance state rather than the off state thereby not causing any loading effect upon crystal 50. Microcontroller 57 selects the power state by monitoring the state of power button 18, via line 69, volume down button 19 via line 80, and volume up button via line 81. A display unit 76 (not shown in FIG. 1) in probe 11 is provided to show the selected power level for probe 11.

Figure 7:
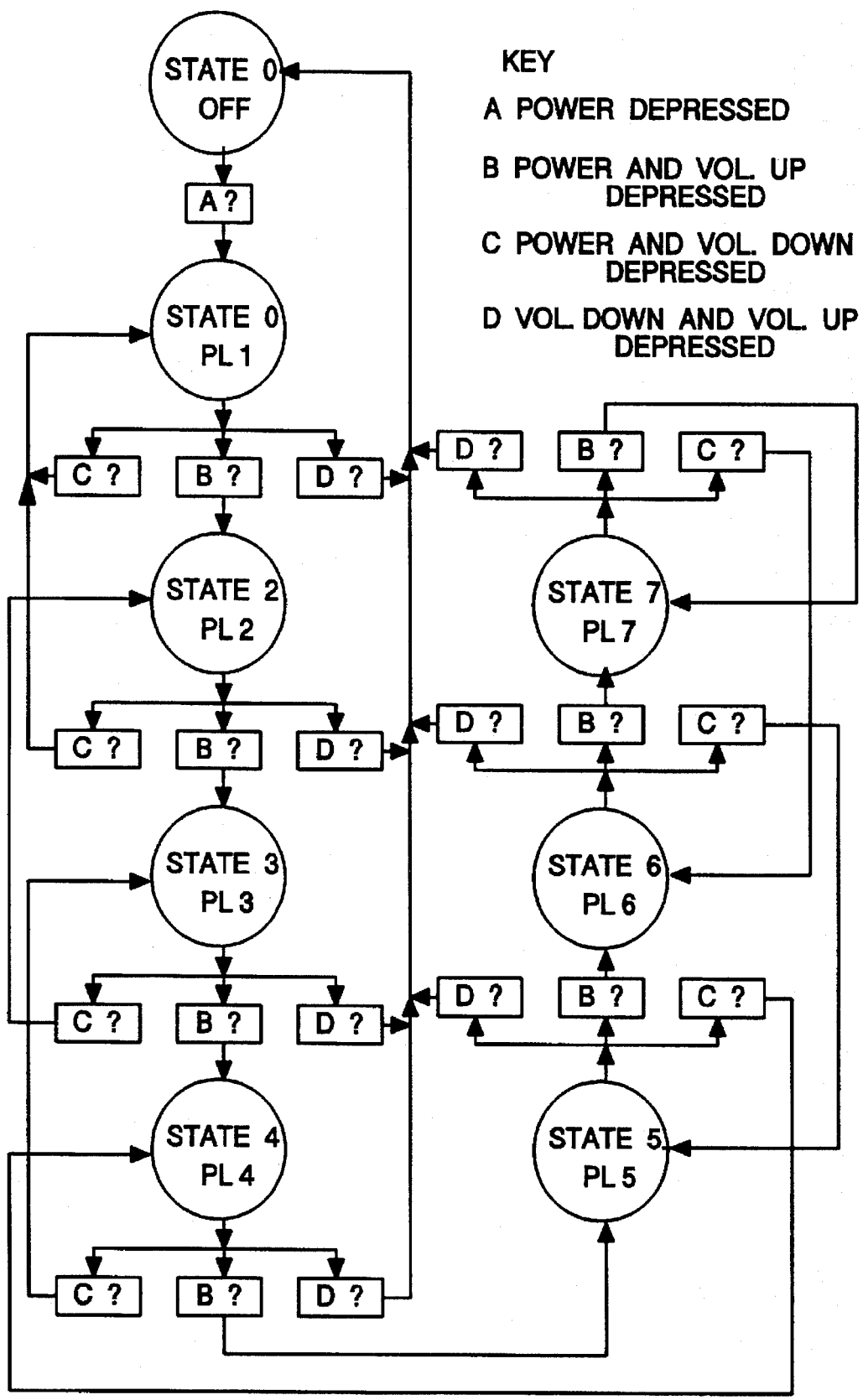
FIG. 7 is a state diagram illustrating the sequence of steps for the selection of one of seven power modes for the probe of the invention.

FIG. 7 is a state diagram for controlling the power level of probe 11 in accordance with commands received via power button 18, volume down button 19 and volume up button 20. In FIG. 7, condition A represents that only power button 18 is depressed; condition B represents that power button 18 and volume up button 20 are simultaneously depressed; condition C represents that power button 18 and volume down button 19 are simultaneously depressed; and condition D represents that volume down button 19 and volume up button 20 are simultaneously depressed.

Again, assume that the microcontroller 57 is in STATE 0, the off state. When microcontroller 57 senses that only the power button 18 is depressed, then microcontroller 57 will switch probe 11 from STATE 0, off, to STATE 1, power level 1. In power level 1 (PL1), microcontroller 57 will initiate a signal on line 19 to turn on drivers 70 and 75 such that crystal 50 is driven with one unit of ultrasonic power. Microcontroller 57 includes a three stage up/down binary counter, which counts from 1 to 7. The count in the up/down counter determines which pairs of drivers are turned by microcontroller 57 via signals on lines 77, 78 and 79. For example, when the up/down counter has a count of five, driver pair 70 and 75 and driver pair 72 and 73 will be turn of thereby by driving crystal 50 with five units of ultrasonic energy.

During Condition B, power button 18 and volume up buttons 20 ar simultaneously depressed, the up/down counter will be continuously stepped up to a maximum count of seven or until either the power button 18 or volume up button 20 is released. The rate of stepping the up/down counter is slow enough such that the user, by observing the power indicator, can stop the count at a desired power level PL1–PL7 for probe 11.

During condition C, power button 18 and volume down button 19 are simultaneously depressed, the up/down counter will be continuously stepped down to a minimum count of one or until either the power button 18 or volume up button 20 is released. The rate of stepping the up/down counter is slow enough such that the user, by observing the power indicator, can stop the count at a desired power level PL7–PL1 for probe 11.

During condition D, volume up button 20 and volume down button 19 are simultaneously depressed, the microcontroller 57 will switch probe 11 from the present power STATE (PL1–PL7) to STATE 0, off, and reset the up/down counter a binary count of 1.

Here the probe 11 can be turned on and off and once tuned on can be stepped up and down between seven power level.

Figure 8:
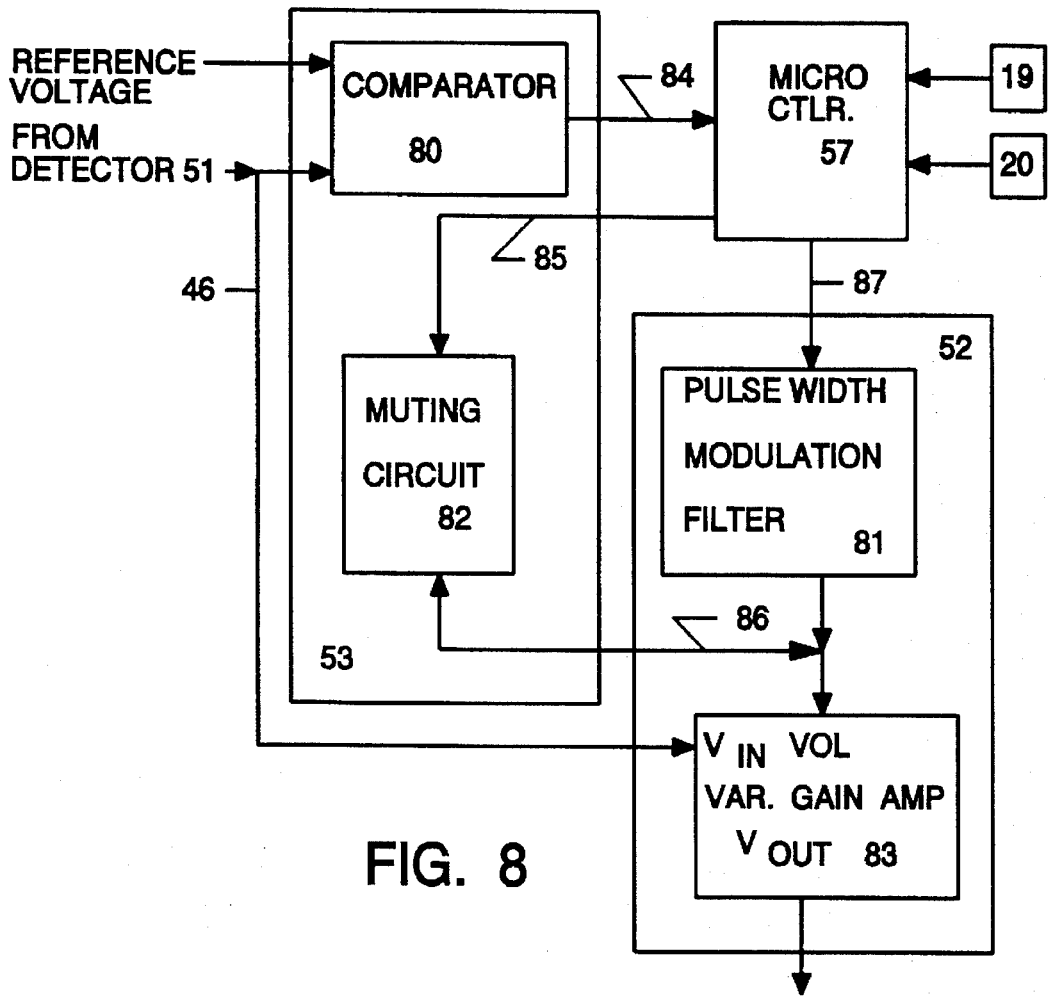
FIG. 8 is a block diagram of the automatic break noise detection and attenuation portion of the probe of the invention.

FIG. 8 is a block diagram of noise controller 53 and the volume controller 52. Noise controller 53 comprises a comparator 18 that monitors the output signal on line 46 of detector 51. The output of comparator 80 will be in a first state whenever the instantaneous magnitude of the output signal from detector 51 is greater than the magnitude of a reference voltage and will be in a second state whenever the instantaneous magnitude of the output signal from detector 51 is less than the magnitude of the reference voltage. As previously stated, break noise is exhibited as a high amplitude signal that is greater in amplitude than the amplitude of the output signal normally expected to be generated by detector 51. Microcontroller 57 monitors the output of comparator 80 and whenever comparator 80 indicates that the output signal from detector 51 is greater than the reference voltage, microcontroller 57 conditions muting circuit 82. Volume controller 52 includes a pulse width modulation filter 81 which generates a gain control voltage on line 86 as a function of the pulse width of the pulse width modulation signal generated by microcontroller 57. Variable gain amplifier 83 gain is controlled by the magnitude of the gain control signal and generates the analog signal provided by probe 11 to headset 10 and Calc. unit 12. Pulse width modulation filter 81 cannot change the gain control voltage fast enough to attenuate the portion of the analog signal associated with the occurrence of break noise in the output signal of detector 51.

Figure 9:
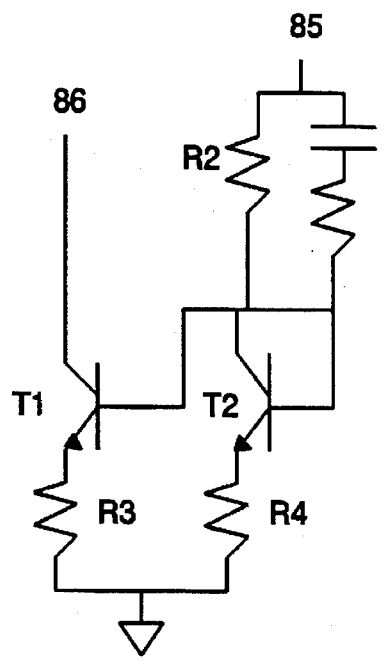
FIG. 9 is a circuit diagram of a current sink circuit of the attenuation portion of the probe of the invention.

FIG. 9 is a circuit diagram of muting circuit 82. Upon detecting the occurrence of break noise, microcontroller 57 generates a voltage on line 85 to muting circuit 82 which effectively, immediately lowers the gain control voltage on line 86 at the output of pulse width modulation filter 81 to variable gain amplifier 83 thereby effectively attenuating the break noise from being emitted through head set 10 or through speaker 14 on Calc. unit 12.

The output of the pulse width modulation filter 81 is connected by line 86 to the collector of transistor T1 via line 86. When the voltage is placed on line 85, transistor T2 controls the current flow through transistor T1 such that transistor T1 acts as a current sink on the output of pulse width modulator filter 81. The muting circuit of is designed to provide two different levels of attenuation during the attenuation period after break noise is detected. Microcontroller 50 has another timer for timing the time that has elapsed since the last break noise has been detected and maintaining the voltage on line 87 to muting circuit 82 until the timer indicates that the attenuation period is over. A typical attenuation period for muting the output signal is 500 ms.

Figure 10:
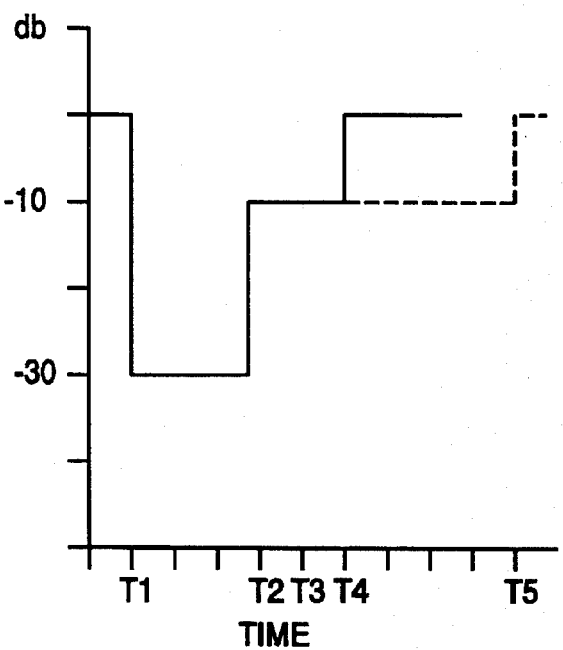
FIG. 10 is a chart illustrating the gain of the variable gain amplifier as a function of the occurrence of break noise is detected.

Referring to FIG. 10, as soon as break noise is detected at T1, the current sink will lower the value of the gain control voltage at the output of the pulse width modulation filter 81 such that the output analog signal of variable gain amplifier 83 will drop by 30 dB. This level of attenuation will change from −30 dB to −10 dB, at time T2, under the control of capacitor C1 and resistor R1. When capacitor C1 is fully charged at T2, the attenuation will be at a level of −10 dB. The period between T1 and T2 is 300 ms. After T2, the attenuation will remain at −10 dB until the timer indicates the end of the attenuation period at T4. Microcontroller 57 will then remove the voltage from the muting circuit, thereby removing the current sink from the output of the pulse width modulator filter 81 and returning the set gain control voltage generated by the pulse width modulation filter 81 to variable gain amplifier 83.

Break noise can occur during an attenuation period. Assume in FIG. 10 that a second occurrence of break noise occurred at time T3. Under this condition the timer for the break noise would be reset for another 500 ms and the attenuation of −10 dB would be held for a full 500 ms until T5 which would be 900 ms after the detection of the first break noise.

While the invention has been particularly shown and described with reference to the preferred embodiments thereof, it will be understood by those skilled in the art that changes in form a detail may be made therein without departing from the spirit and scope of the invention. Given the above disclosure of general concepts and specific embodiments, the scope of the protection sought is defined by the following.

What is claimed is:

1. A noise controller for use in a probe in a hand held ultrasonic Doppler fetal heart beat detection and monitoring system, said probe including a crystal for generating an input signal as a function of the ultrasonic energy in received ultrasonic wave and a detector for generating a first signal from said input signal, said noise controller comprising:

a volume controller for receiving said first signal and for processing said first signal to produce an analog signal as the output of said probe, a detector for generating a second signal whenever break noise is detected in said first signal;

a muting means connected to said volume controller and said detector for immediately lowering the amplitude of said analog signal upon detection of said break noise by said detector sensor to substantially attenuated in said analog signal said break noise which occurred in said first signal.

2. The noise controller of claim 1 wherein said detector comprising:

a comparator for continuously comparing the amplitude of said first signal with a reference signal where said reference signal has a value greater than the amplitude of the first signal without break noise and less than the amplitude of the first signal with break noise and for generating said second signal having a first value when said amplitude of said first signal is greater than said amplitude of said reference signal and a second value when said amplitude of said first signal is less than said amplitude of said reference signal.

3. The noise controller of claim 2 wherein said muting means comprises:

a microcontroller for monitoring said second signal and for generating a mute signal when said first signal changes from said second value to said first value, said mute signal causing the amplitude of said analog signal to be immediately decrease for a specified period of time.

4. The noise controller of claim 3 wherein:

said volume controller comprises:

a volume generator having an output and for generating at said output a gain signal in response to volume signals received from said microcontroller;

a variable gain amplifier whose gain is a function of said gain signal and for receiving and processing said first signal to generate said analog signal; and said muting means further comprising:

a muting circuit connected to said output of said volume generator means for immediately reducing the value of said gain signal to said variable gain amplifier upon the detection of break noise by said detector and for maintaining said reduced gain during the period of time that said microcontroller generates said mute signal.

5. The noise controller of claim 4 wherein said muting circuit will decrease said amplitude of said analog signal by a first amount for a first period immediately upon the issuing of said mute signal by said microcontroller and then thereafter by a second amount until said mute signal is discontinued by said microcontroller.

6. The noise controller of claim 1 wherein said muting means comprises:

a microcontroller for monitor said second signal for determining the presence of break noise and for generating a signal which will cause the amplitude of said analog signal to be immediately decrease for a specified period of time.

7. A method of attenuating break noise detected by a probe in a hand held ultrasonic Doppler fetal heart beat detection and monitoring system, step method comprising the steps of:

generating a first signal as a function of the ultrasonic energy of ultrasonic waves received by said probe;

generating an analog signal from said first signal;

sensing the occurrence of break noise in said first signal;

attenuating immediately upon sensing the occurrence of break noise in said first signal the amplitude of an analog signal for a specific period of time from the sensing of each occurrence of said break noise.

* * * * *

UNITED STATES PATENT AND TRADEMARK OFFICE
CERTIFICATE OF CORRECTION

PATENT NO. : 5,630,418
DATED : May 20, 1997
INVENTOR(S) : William C. Lee et al.

It is certified that error appears in the above-indentified patent and that said Letters Patent is hereby corrected as shown below:

Column 1, line 27, "mothers" should be --mother's--;

Column 1, line 29, "mothers" should be --mother's--;

Column 3, line 46, "enters" should be --enter--;

Column 3, line 46, "mothers" should be --mother's--;

Column 4, line 7, "increase" should be --increased--;

Column 4, line 27, "a" should be --an--;

Column 4, line 61, "drive" should be --driver--;

Column 5, line 32, after "microcontroller" insert --57--;

Column 5, line 36, "downbutton" should be --down button--;

Column 7, line 7, after "turned" insert --on--;

Column 7, line 10, "turn" should be --turned--;

Column 7, line 11, "of thereby" should be --on thereby--;

Column 7, line 14, "ar" should be --are--;

Column 7, line 35, "tuned" should be --turned--;

Column 7, line 55, after "of the pulse width" delete the second occurrence of "of the pulse width";

UNITED STATES PATENT AND TRADEMARK OFFICE
CERTIFICATE OF CORRECTION

PATENT NO. : 5,630,418
DATED : May 20, 1997
INVENTOR(S) : William C. Lee et al.

It is certified that error appears in the above-indentified patent and that said Letters Patent is hereby corrected as shown below:

Column 8, line 10, "of" should be --82--;

Column 8, line 45, "a" should be --and--;

Column 8, line 65, "attenuated" should be --attenuate--;

Column 9, line 19, "decrease" should be --decreased--;

Column 10, line 14, "monitor" should be --monitoring--;

Column 10, line 17, "decrease" should be --decreased--.

Signed and Sealed this

Eighteenth Day of August, 1998

Attest:

Attesting Officer

BRUCE LEHMAN

Commissioner of Patents and Trademarks